(12) United States Patent
Johnston et al.

(10) Patent No.: US 11,172,847 B2
(45) Date of Patent: Nov. 16, 2021

(54) PORTABLE LASER SYSTEM FOR MEASURING HEIGHT OF A HUMAN SUBJECT

(71) Applicant: Arizona Board of Regents on behalf of Arizona State University, Scottsdale, AZ (US)

(72) Inventors: Carol Johnston, Mesa, AZ (US); Sandra Mayol-Kreiser, Gilbert, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 340 days.

(21) Appl. No.: 16/217,582

(22) Filed: Dec. 12, 2018

(65) Prior Publication Data
US 2019/0183386 A1 Jun. 20, 2019

Related U.S. Application Data

(60) Provisional application No. 62/598,105, filed on Dec. 13, 2017.

(51) Int. Cl.
*A61B 5/107* (2006.01)
*G01B 11/06* (2006.01)
*A61B 5/00* (2006.01)

(52) U.S. Cl.
CPC .......... *A61B 5/1079* (2013.01); *A61B 5/0004* (2013.01); *A61B 5/1072* (2013.01);
(Continued)

(58) Field of Classification Search
CPC .......... G06T 2207/30196; G06T 17/00; A61B 5/107; A61B 5/1079; A61B 5/0004;
(Continued)

(56) References Cited

U.S. PATENT DOCUMENTS

| 7,200,952 B2 | 4/2007 | Montagnino | |
|---|---|---|---|
| 2005/0155246 A1* | 7/2005 | Montagnino | ........ A61B 5/4869 33/832 |

(Continued)

OTHER PUBLICATIONS

Acuity., "Laser Rangefinders are used to Measure Human Height" [online], Human Height Measuring, 2014 [retrieved on Jul. 16, 2019 from archive.org, as it appeared on May 28, 2017], retrieved from the internet: <URL:https://web.archive.org/web/20170528193730/https://www.acuitylaser.com/products/category/human-height-measuring/>.

(Continued)

*Primary Examiner* — Patrick Fernandes
(74) *Attorney, Agent, or Firm* — Withrow & Terranova, P.L.L.C.

(57) ABSTRACT

A portable laser height measuring system including an upper assembly including an elongated top flat plate attached to an upper back plate, wherein the elongated top flat plate includes a top side and an underside is disclosed herein. A separate lower assembly including a base is attached to a bottom backplate. A laser measurement device is affixed to the elongated top flat surface. A leveling device is mounted at one end of the elongated top flat plate proximate the laser measurement device; and a data collection device is electronically coupled to receive signals from the laser measurement device.

15 Claims, 8 Drawing Sheets

(52) U.S. Cl.
CPC .......... *A61B 5/6814* (2013.01); *A61B 5/6829* (2013.01); *G01B 11/0608* (2013.01); *A61B 2562/0233* (2013.01)

(58) Field of Classification Search
CPC ... A61B 5/1072; A61B 5/0077; A61B 5/6814; A61B 5/6829; A61B 2562/0233; G01B 11/0608
See application file for complete search history.

(56) References Cited

U.S. PATENT DOCUMENTS

| | | | |
|---|---|---|---|
| 2011/0167658 A1* | 7/2011 | Chul | A61B 5/1072 33/512 |
| 2012/0065916 A1* | 3/2012 | Staats | A61B 5/1079 702/97 |

OTHER PUBLICATIONS

Canda, A., "Stature Estimation from Body Segment Lengths in Young Adults—Application to People with Physical Disabilities", Journal of Physiological Anthropology, Mar. 2009, vol. 28, No. 2, pp. 71-82 <DOI:10.2114/jpa2.28.71>.

Chen, W-Y. et al., "The non-contact human-height measurement scheme", International Conference on Machine Learning and Cybernetics (Guilin, China, Jul. 10-13, 2011), 2011 (date added to IEEE Xplore: Jul. 2011), pp. 572-575 <DOI:10.1109/ICMLC.2011.6016821>.

De Onis, M., "The use of anthropometry in the prevention of childhood overweight and obesity", International Journal of Obesity, Nov. 2004, vol. 28, pp. S81-S85 <DOI:10.1038/sj.ijo.0802810>.

Deuerenberg, P. et al., "Body mass index as a measure of body fatness: age- and sex-specific prediction formulas", British Journal of Nutrition, Mar. 1991, vol. 65, No. 2, pp. 105-114 <DOI:10.1079/BJN19910073>.

Dietz, W. et al., "Introduction: the use of body mass index to assess obesity in children", American Journal of Clinical Nutrition, Jul. 1999, vol. 70, No. 1, p. 123S-125S <DOI:10.1093/ajcn/70.1.123s>.

Duggan, M., "Anthropometry as a tool for measuring malnutrition: impact of the new WHO growth standards and reference", Annals of Tropical Paediatrics, Mar. 2010, vol. 30, No. 1, pp. 1-17 <DOI:10.1179/146532810X12637745451834.>.

Foster, B. et al., "Development and validation of a predictive equation for lean body mass in children and adolescents", Annals of Human Biology, May 2012, vol. 39, No. 3, pp. 171-182 <DOI:10.3109/03014460.2012.681800>.

Frankenfield, D. et al., "Prediction of resting metabolic rate in critically ill patients at the extremes of body mass index", Journal of Parenteral and Enteral Nutrition, May-Jun. 2013 [available online Aug. 2012], vol. 37, No. 3, pp. 361-367 <DOI:10.1177/0148607112457423.>.

Froehlich-Grobe, K. et al., "Measuring Height Without a Stadiometer: Empirical Investigation of Four Height Estimates Among Wheelchair Users", American Journal of Physical Medicine & Rehabilitation, Aug. 2011, vol. 90, No. 8, pp. 658-666 <DOI:10.1097/PHM.0b013e31821f6eb2>.

Haapala, H. et al., "Agreement Between Actual Height and Estimated Height Using Segmental Limb Lengths for Individuals with Cerebral Palsy", American Journal of Physical Medicine & Rehabilitation, Jul. 2015, vol. 94, No. 7, pp. 539-546 <DOI:10.1097/PHM.0000000000000205>.

Kacer, M. et al., "Effect of inspiration/expiration on height measurement", Journal of Pediatric Endocrinology and Metabolism, Aug. 2008, vol. 21, No. 8, pp. 763-769.

Kleijn, W. et al., "Measuring the height at the withers of ponies at a competition and at home using a laser device", The Veterinary Journal, Nov. 2009 (available online Aug. 2008), vol. 182, No. 2, pp. 193-197 <DOI:10.1016/j.tvjl.2008.07.007>.

Kusnoto, B. et al., "Reliability of a 3D surface laser scanner for orthodontic applications", American Journal of Orthodontics and Dentofacial Orthopedics, Oct. 2002, vol. 122, No. 4, pp. 342-348 <DOI:10.1067/mod.2002.128219>.

Mayol-Kreiser, S. et al., "Examining the utility of a laser device for measuring height in free-living adults and children", Nutrition Journal, Sep. 2015, vol. 14, No. 93, 5 pages <DOI:10.1186/s12937-015-0082-4>.

Rannisto, S. et al., "Measurement of leg-length discrepancy using laser-based ultrasound method", Acta Radiologica, Dec. 2011 [available online Nov. 2011], vol. 52, No. 10, pp. 1143-1146 <DOI:10.1258/ar.2011.110268>.

Routen, A. et al., "The impact of school-day variation in weight and height on National Child Measurement Programme body mass index-determined weight category in Year 6 children", Child: Care, Health and Developmment, May 2011 [available online Jan. 2011], vol. 37, No. 3, pp. 360-367 <DOI:10.1111/j.1365-2214.2010.01204.x>.

Moss, L. et al., "The reliability of height measurement (the Wessex Growth Study)", Archives of Disease in Childhood, Dec. 1990, vol. 65, No. 12, pp. 1340-1344 <DOI:10.1136/adc.65.12.1340>.

Wijnhoven, T. et al,. "WHO European Childhood Obesity Surveillance Initiative 2008: weight, height and body mass index in 6-9-year-old children", Pediatric Obesity, Apr. 2013 [available online Sep. 2012], vol. 8, No. 2, pp. 79-97 <DOI:10.1111/j.2047-6310.2012.00090.x>.

* cited by examiner

PORTABLE LASER SYSTEM FOR MEASURING HEIGHT OF A HUMAN SUBJECT

STATEMENT OF RELATED APPLICATIONS

This application claims priority to U.S. Provisional Patent Application No. 62/598,105 filed on Dec. 13, 2017, wherein the entire disclosure of the foregoing application is hereby incorporated by reference herein.

TECHNICAL FIELD

The present invention relates to a method and system for measuring height of adults and children. More particularly, the method and system are directed to measuring height of human subjects using a two-piece portable automated laser stadiometer.

BACKGROUND

Height is an important health assessment measure with many applications. For example, height is used to calculate body mass index, the most commonly applied metric for placing individuals and populations in weight categories. Height is also used to assess growth and nutritional adequacy in children, and it is used in predictive equations to estimate other health parameters including metabolic rate and lean body mass.

In research and field settings, height is typically measured with a stadiometer, a portable device composed of a vertical backboard and adjustable head piece, with a reported measurement error of 0.2-0.3 cm. Commercially available stadiometers are relatively bulky, hard to transport and expensive. There currently exists a need for a lighter weight, less cumbersome device for measuring height to promote health benefits in Third World countries and similarly situated communities. For example, in 2016, UNICEF spent about 60 million dollars on about 125,000 devices and would most likely benefit from a less costly, accurate and more compact system.

The present invention overcomes several deficiencies of the known state-of-the-art. As compared to commercially available stadiometers, the portable laser height measuring system disclosed herein for the first time is easier to use, accurate, less costly (with a sale price of about $500 versus $300-$1000 for commercial devices), small and lightweight (<200 g; 42×15×12 cm versus >2 kg; 70×43×6 cm when folded for existing stadiometers), and is more versatile as it can measure both standing height and supine height. Further, utilizing a laser system to measure height would reduce the common sources of error in this measurement (e.g. error in reading the mark on the ruler and error in the assembly of a measuring stick as typically used in most currently available portable stadiometers).

BRIEF SUMMARY OF THE DISCLOSURE

This summary is provided to introduce, in a simplified form, a selection of concepts that are further described below in the Detailed Description. This summary is not intended to identify key features of the claimed subject matter, nor is it intended to be used as an aid in determining the scope of the claimed subject matter.

A portable laser height measuring system including an upper assembly including an elongated top flat plate attached to an upper back plate, wherein the elongated top flat plate includes a top side and an underside is disclosed herein. A separate lower assembly including a base is attached to a bottom backplate (e.g., a lower assembly that is not physically connected to the upper assembly). A laser measurement device is affixed (e.g., removably affixed or coupled) to the elongated top flat surface. A leveling device is mounted at one end of the elongated top flat plate proximate the laser measurement device; and a data collection device is electronically coupled to receive signals from the laser measurement device.

In one example, a target indentation is manufactured into the end of the elongated bottom flat plate to guide the laser measurement perpendicular to the ground; and a data collection device is electronically coupled to receive signals from the laser measurement device.

BRIEF DESCRIPTION OF THE DRAWINGS

While the novel features of certain embodiments of the invention are set forth with particularity in the appended claims, the invention, both as to organization and content, will be better understood and appreciated, along with other objects and features thereof, from the following detailed description taken in conjunction with the drawings, in which:

Figure 1:
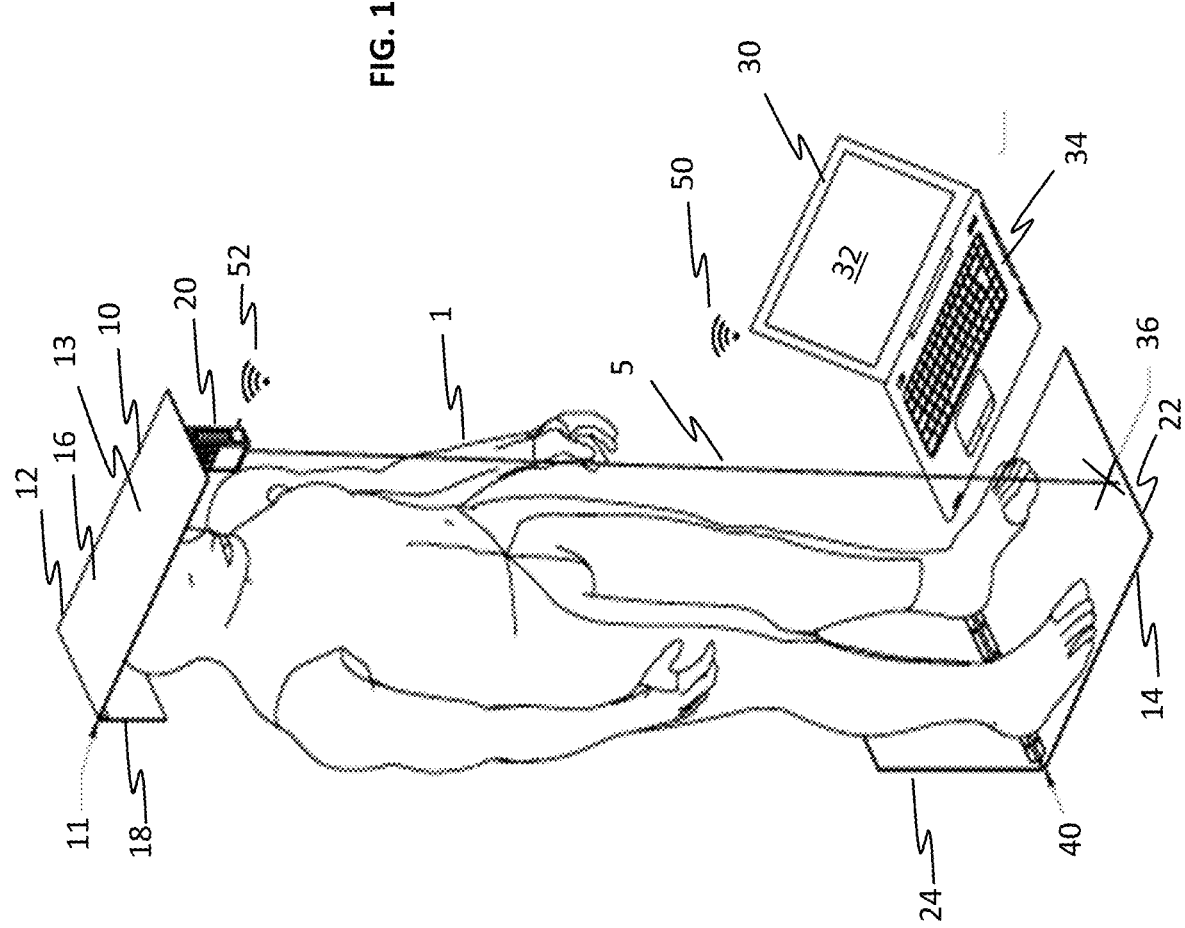
FIG. 1 schematically shows an example of a portable laser height measuring system.

In the drawings, identical reference numbers identify similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION

The following disclosure describes a method and system for height measurement of a human subject. Several features of methods and systems in accordance with example embodiments are set forth and described in the figures. It will be appreciated that methods and systems in accordance with other example embodiments can include additional procedures or features different than those shown in the figures. Example embodiments are described herein with respect to a method and system directed to an automated laser stadiometer. However, it will be understood that these examples are for illustrating the principles, and that the invention is not so limited.

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one example," "an example embodiment," "one embodiment," "an embodiment" or combinations and/or variations of these terms means that a particular feature, structure or characteristic described in connection with the embodiment or example is included in at least one embodiment or example of the present disclosure. Thus, the appearances of the phrases "in one example" or "in an example" in various places throughout this specification are not necessarily all referring to the same example embodiment or example. Furthermore, the particular features, structures, or characteristics may be combined in any suitable manner in one or more embodiments or examples.

Definitions

Generally, as used herein, the following terms have the following meanings; The articles "a" or "an" and the phrase "at least one" as used herein refers to one or more.

"Bluetooth®" technology, as used herein means a commercially available low-power wireless connectivity technology used to stream audio, transfer data and broadcast information between devices. This technology is available from Bluetooth SIG, Inc. of Kirkland, Wash.

As used herein the "Frankfort plane" is used in its generally accepted meaning as a plane used in craniometry that is determined as the highest point on the upper margin of the opening of each external auditory canal and the low point on the lower margin of the left orbit, and that is used to orient a human skull or head usually so that the plane is horizontal—also eye-ear plane, Frankfort horizontal, or Frankfort plane.

As used herein, "plurality" is understood to mean more than one. For example, a plurality refers to at least two, three, four, five, ten, 25, 50, 75, 100, 1,000, 10,000 or more.

As used in this specification, the terms "computer", "processor" and "computer processor" encompass a personal computer, a tablet computer, a smart phone, a microcontroller, a microprocessor, a field programmable object array (FPOA), a digital signal processor (DSP), an application-specific integrated circuit (ASIC), a field programmable gate array (FPGA), a programmable logic array (PLA), or any other digital processing engine, device or equivalent capable of executing software code including related memory devices, transmission devices, pointing devices, input/output devices, displays and equivalents.

"Obtaining" is understood herein as manufacturing, purchasing, or otherwise coming into possession of.

The portable laser height measurement system disclosed herein features several advantages over currently available portable stadiometer devices. Laser measurements are accurate, reproducible, rapid, and versatile. A laser device's digital output can be transferred to different devices using, for example, Bluetooth® technology. In clinical and research units, a laser may be mounted for ease of use, and a hand-held version can easily be adapted for use in the field. Moreover, the portable laser height measurement system disclosed herein is capable of measuring individuals in a supine position as well as a standing position, a feature not available with stadiometers.

Referring now to FIG. 1, an example of an automated portable height measuring system is schematically shown. A laser height measuring system 10 includes an upper assembly 12 and a separate (e.g., physically unconnected) lower assembly 14. The upper assembly 12 includes a laser measurement device 20 affixed to an elongated top flat plate 16. The top flat plate 16 is preferably movably (e.g., foldably or hingedly) attached to a top vertical backplate 18. The lower assembly 14 comprises a base plate 22 that in certain embodiments may be movably (e.g., foldably or hingedly) attached to a bottom vertical back plate 24. A leveling device 13 is also mounted at one end of the elongated top flat plate 16 proximate the laser measurement device 20. A data collection device 30 includes a display 32 and an input apparatus 34. The data collection device may be adapted to be wirelessly connected to the laser and other devices as indicated by wireless symbol 50.

In one useful example, the base plate 22 may also include a laser measurement target 36, such as a bull's-eye, crosshairs or the like. In one example, a target indentation is manufactured into the end of the elongated bottom flat plate to guide the laser measurement perpendicular to the ground; and a data collection device is electronically coupled to receive signals from the laser measurement device.

The laser measurement device 20, may be any commercially available laser measurement device suitable for removably mounting to the upper assembly. When activated, the laser measurement device 20 generates a laser beam 5. The upper assembly 12 may include a hinge 11 (or one or more of such hinges) for foldably coupling the top flat plate 16 to the top vertical component 18. Similarly, the base plate 22 may be coupled to the bottom vertical back plate 24 with a bottom hinge 40. In this way, the upper assembly 12 and the separate lower assembly 14 may each be folded for compact storage and transport—a significant advantage compared to existing height-measurement technologies. In one useful example, both the upper assembly 12 and lower assembly 14 have back plates adapted to be positioned perpendicular to the main plates with stainless steel hinges that permit folding for travel or for storage.

Figure 4:
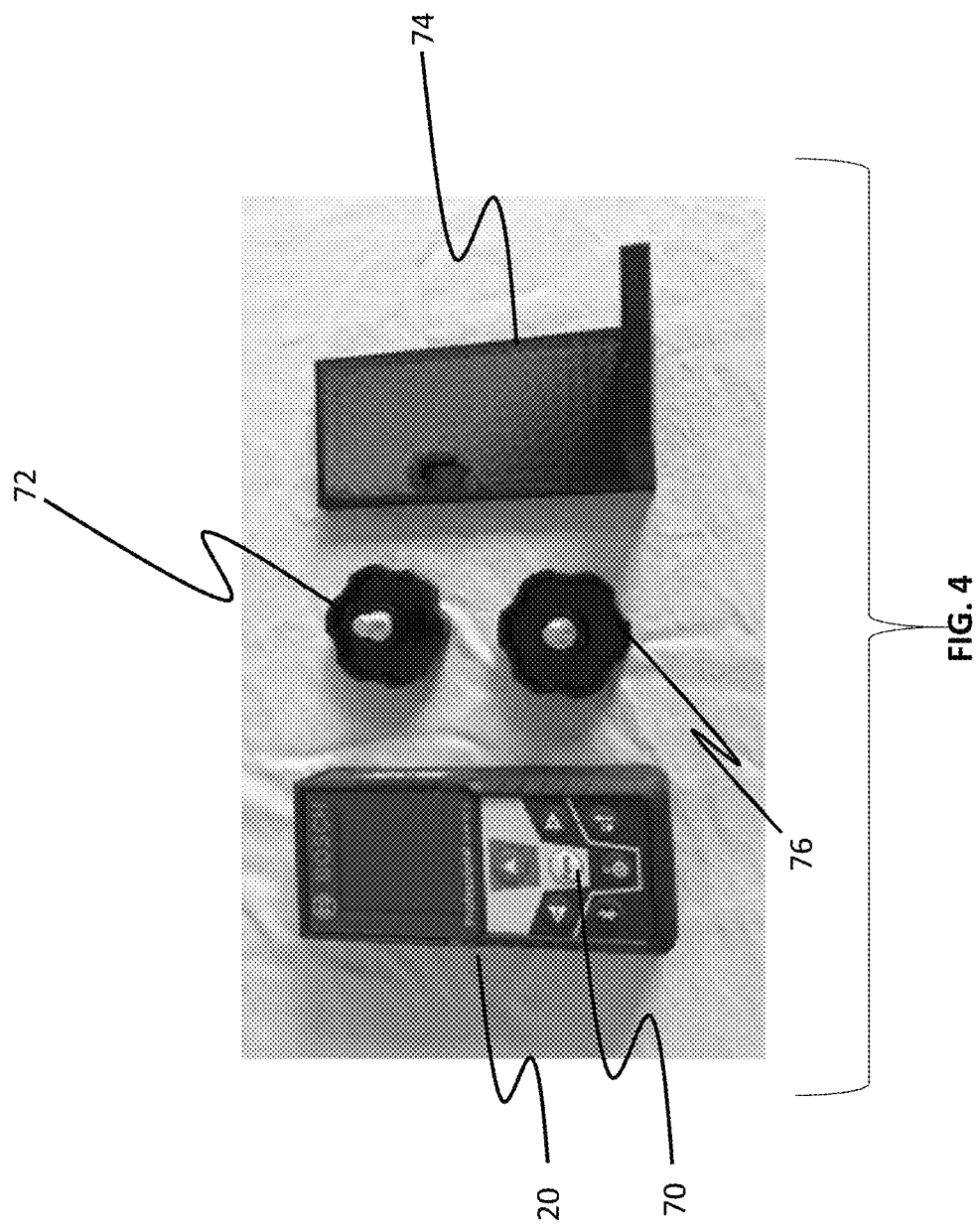
FIG. 4 shows an example of components employed in the portable laser height measuring system including a portable laser measurement device with a mounting base and assembly knobs.

The laser may comprise a separate device that is designed with a conventionally fabricated base (as shown in FIG. 4) adapted to lock into position on the top assembly, and allow removal for storing separately or for travel.

Laser measurement device 20 may be any commercially available laser measurement device and may advantageously include Bluetooth® communication, other wireless communication components and the like as indicated by wireless symbol 52. Similarly, the data collection device may be, for example, a personal computer, smart phone or laptop computer that is also Bluetooth® enabled. In this way wireless communication between the laser measurement device 20 and the data collection device 30 is enabled. Those skilled in the art having the benefit of this disclosure will recognize that other wireless transmission schemes may also be useful in the invention is not limited to Bluetooth® enabled transmissions.

Having described the components of portable laser height measuring system 10, an explanation of the system in operation is provided hereinbelow for promoting further understanding of the system. In one example, the laser height measuring system comprises at least a two-part system. A third component may comprise a data collection device, such as a portable computer or the like.

The manufacturing process may advantageously employ moldable plastic that is substantially impervious to normal wear, extreme temperatures, and water. The components may be made using standard plastic molding techniques, extrusions, 3D printing and equivalents thereof. In one example, the back plates of each assembly are composed of acrylonitrile butadiene styrene (ABS) or similar plastic polymers and the base plate 22 and top flat plate 16 are made from polyethylene. In one example a device weighs about 4.1 kg and fits into a backpack.

In another example, the upper assembly was fabricated from a 57×12 cm aluminum plate (2.5 mm thick) bent at a 90-degree angle at the 15 cm mark. In this example, the two-part system including the upper and lower assemblies weighed about 190 grams.

Still referring to FIG. 1, the upper assembly is placed on top of the head with the shorter surface positioned against a wall. A laser is mounted at the end of the elongated top surface pointed toward the ground. The leveler 13 is also mounted at the end of the elongated top plate to assure the laser measuring device is reading vertical height. The upper assembly is leveled on the head with the laser measuring device in place. The lower device can be used with the test subject 1 standing vertically with her feet on the base plate 22.

The laser measuring device may have its projected beam 5 aligned with the target 36. For standing height measure, an individual can stand against a wall or be free-standing. If a wall is used, the base is placed on the floor with the back plate 24 placed vertically against the wall. Shoes are removed. The individual is positioned with their back to the wall and feet on the base with heels touching firmly against the back plate. The back of the head, shoulder blades, and buttocks should also touch the wall. Any objects obscuring the top of the head are to be removed including hats, buns, braids, or hair accessories and the individual is instructed to stand straight with hands at side and body weight evenly distributed to both feet. The upper assembly 12 is positioned on the top of the head with the upper back plate 18 behind the individual's head and against the wall; the laser measuring device on the top plate is pointed to the ground in front of the individual. The individual's head is adjusted to align with the Frankfort plane (i.e., a line horizontal to the floor from the ear canal to the lower border of the orbit of the eye) and the laser measuring device can then be turned on and its beam directed to the bullseye on the foot-piece. The individual can be told to stand as tall as possible, take a deep breath, and hold this position. The measurement is taken by pushing a button on the laser, for example (See FIG. 4). The measurement may advantageously be taken in triplicate and averaged.

If a height measurement is taken with a free-standing subject, substantially the same procedure is followed: the individual is positioned on the base with heels touching firmly against the back plate. The individual should stand straight as detailed above, and the upper assembly is placed on the head with the inside of the back plate against the back of the head and the laser measuring device pointing downward in front of the individual. The head is adjusted to the Frankfort plane and the laser measuring device turned on with its beam directed to the bullseye on the foot-piece. The measurement is taken by pushing a button on the laser, for example. The measurement is taken in triplicate and averaged.

Figure 2:
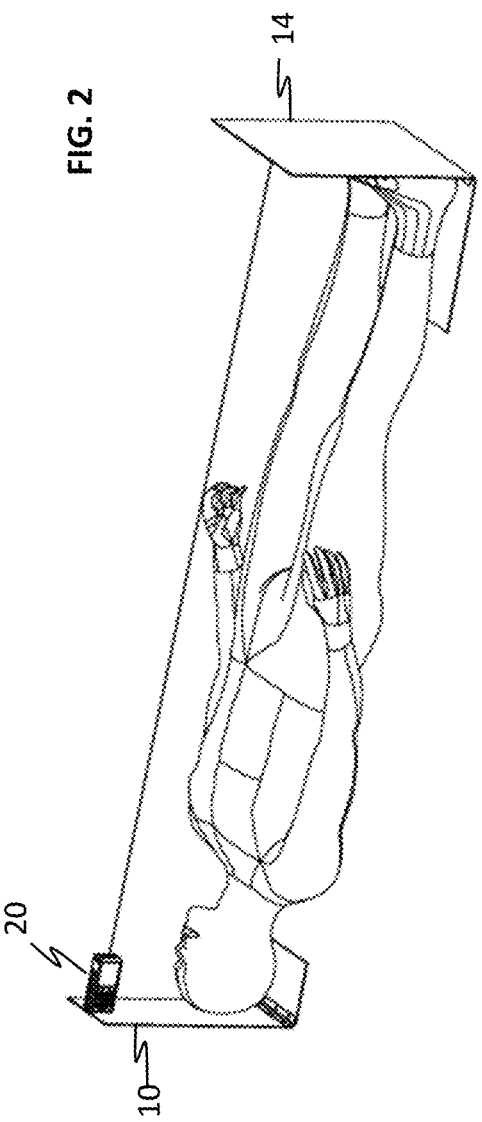
FIG. 2 schematically shows an example of a portable laser height measuring system used to measure the height of a supine subject.

Referring now briefly to FIG. 2, an example of a portable automated height measuring system used to measure the height of a supine subject is schematically shown. Supine measurements are conducted substantially similarly as described above, however with the subject 1 lying flat on their back. Shoes are removed, and any objects obscuring the top of the head are removed including hats, buns, braids, or hair accessories. The feet are flexed at a 90° angle and the foot-piece is placed under the feet with the back plate resting on the ground and the bottom plate at a 90° angle to the ground. Hands are to the side, and the individual is told to look skyward with the Frankfort plane perpendicular to the ground. The laser light is pointed at the bullseye on the foot-piece, and the measurement is taken in triplicate and averaged. In certain embodiments, the presence of the foot-piece constitutes a significant advantage compared to existing height-measurement technologies, the latter of which cannot be used to accurately measure the height of an individual in the supine position.

Assembly Instructions and System Information

One example of a laser measurement device as disclosed herein is now being made by the inventors herein using the facilities of MASTRIK LLC, Tempe Ariz., USA, under the brand name LAHI™. The LAHI™ device is a two piece device including an upper assembly (15.2×41.6 cm, 1.3 kg) that is placed on the head (either standing or supine) and a lower assembly (33×43.2 cm, 2.8 kg) that is placed under the feet. The LAHI™ device assemblies fold to a 5 cm thickness and can be placed into a backpack for transport. The materials are a durable plastic and easy to clean, and the hinges and hardware are stainless steel.

The LAHI™ model device provides height/length measurements of infants, children and adults (range 30-215 cm) with a laser range of 46-215 cm. The LAHI™ model device has a digital output in cm with one decimal digit; display is not reliant on electrical power sources since the device uses standard batteries or rechargeable batteries. In one example, detachable laser measurement device 20 may comprise a commercially available portable laser measurement device, as, for example, Bosch model Blaze™ laser GLM 50 C, available from Robert Bosch Tool Corporation, Mt. Prospect, Ill., USA. The Bosch model laser has a backlit color screen for easy reading, and the user can cycle through functions to switch between units of measure (e.g., cm vs. inches). The last 30 measurements are automatically stored. The device can be used against a wall, freestanding, or in a supine position. The laser beam is directed at the target on the lower assembly, and a function button 70 can be pushed to initiate a measurement (e.g. eliciting a beep). The measurement is displayed in an easy-to-read digital format (two decimals) and can be downloaded to a portable device such smart phone, portable computer, tablet, etc. As manufactured in one example, the device weighs less than 6 kilo and can be carried by one person. The LAHI™ device weighs 4.1 kg. When folded for storage and transport, the device dimensions are 33×43.2×5 cm, and the device can be placed in a backpack. Subjects can be positioned, measured, and readings documented accurately by 2 persons. The device can be operated by non-technical users with 1 day of training or less. Training entails (a) practice aligning the upper assembly in standing or supine individuals so that the laser light hits the target on the lower assembly and (b) learning the operation of the laser. A user can use one hand to hold the upper assembly of the device steady, and the second hand operates the laser (e.g., pressing a single button). If there is a major height differential between the technician and the individual a stool or step ladder may be employed.

Accuracy of the portable height measurement system was +/−3 mm when static objects of 55, 120, 210 cm were measured. Research conducted on an earlier version (2G) of this device demonstrated the accuracy of measurement (1.13-1.27 mm) and the precision when compared directly to a stadiometer method (intraclass correlation, r=0.993-0.998). Precision of device was +/−2 mm representing the ability of the device to produce the same result repeatedly.

Figure 3:
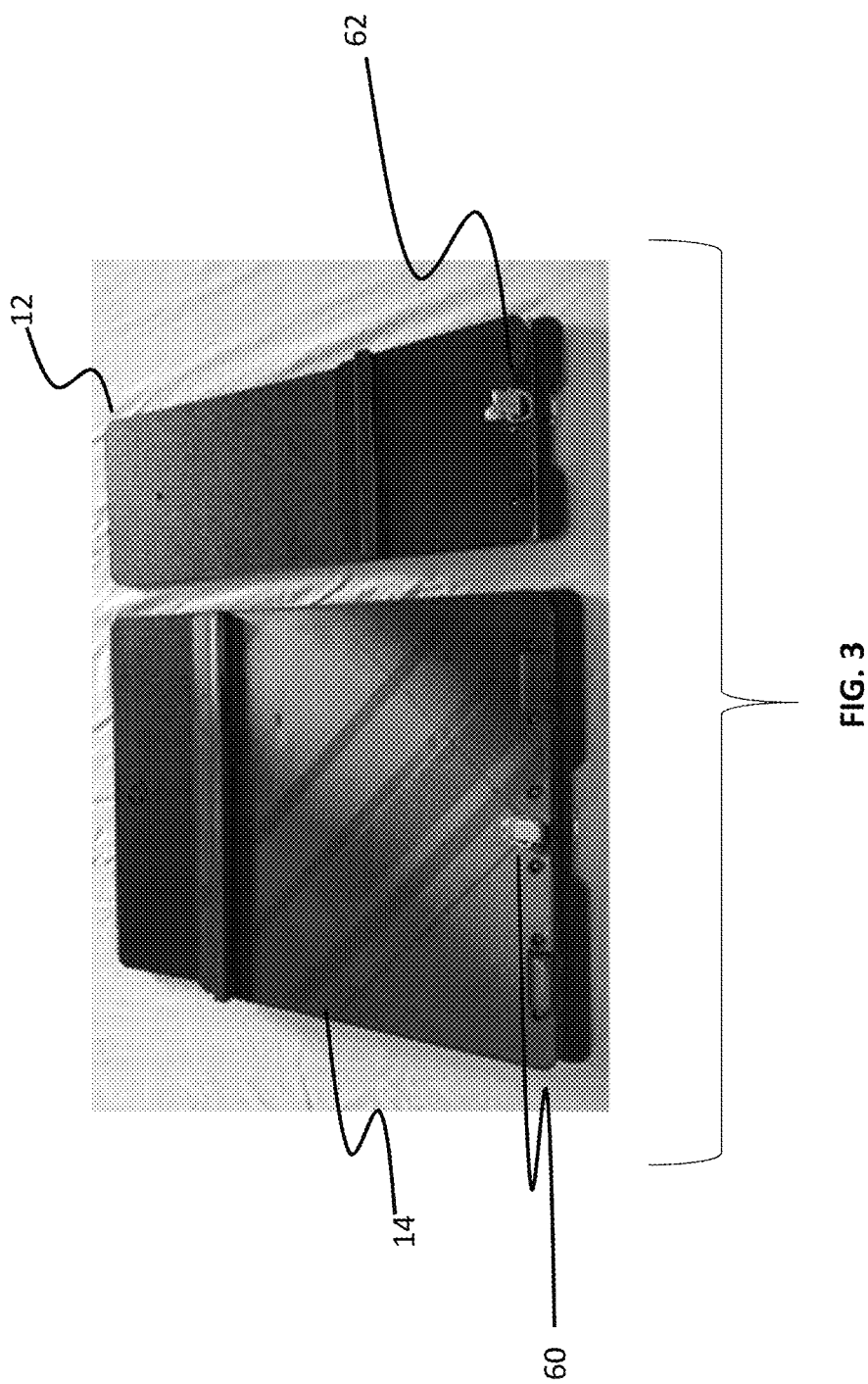
FIG. 3 shows an example of upper and lower assemblies in a closed position.

Referring now to FIG. 3, unassembled device components are shown. The lower assembly 14 and the upper assembly 12 are each shown in the closed position. Each assembly includes an attached draw latch 60, 62 respectively.

Referring now to FIG. 4, an example of components employed in the portable laser height measuring system including a portable laser measurement device with a mounting base and assembly knobs is shown. As described below, a first threaded knob 72 is adapted to attach a laser mounting base 74 to the upper assembly 12. A second threaded knob 76 is used to attach the laser measurement device 22 the mounting base 74.

Figure 5:
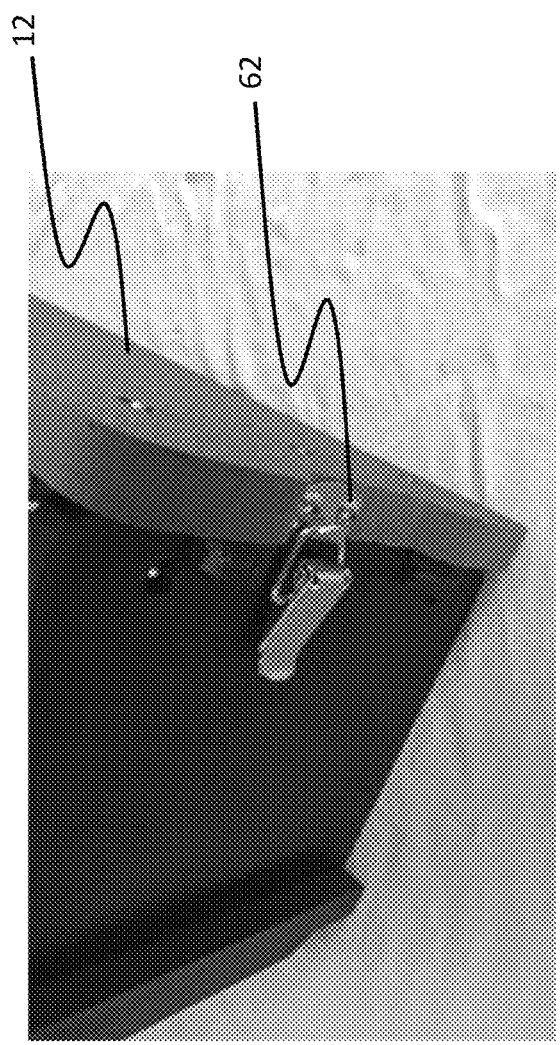
FIG. 5 shows an example of a draw latch used to open an upper assembly.

Referring now to FIG. 5, an example of a draw latch used to open an upper assembly is shown. During assembly, a user may open upper assembly 12 and fasten the draw latch 62 to secure a 90° angle between plates 16, 18. Referring briefly again to FIG. 3, draw latch 60 may similarly be used to secure a 90° angle between the plates of the lower assembly 14.

Figure 6:
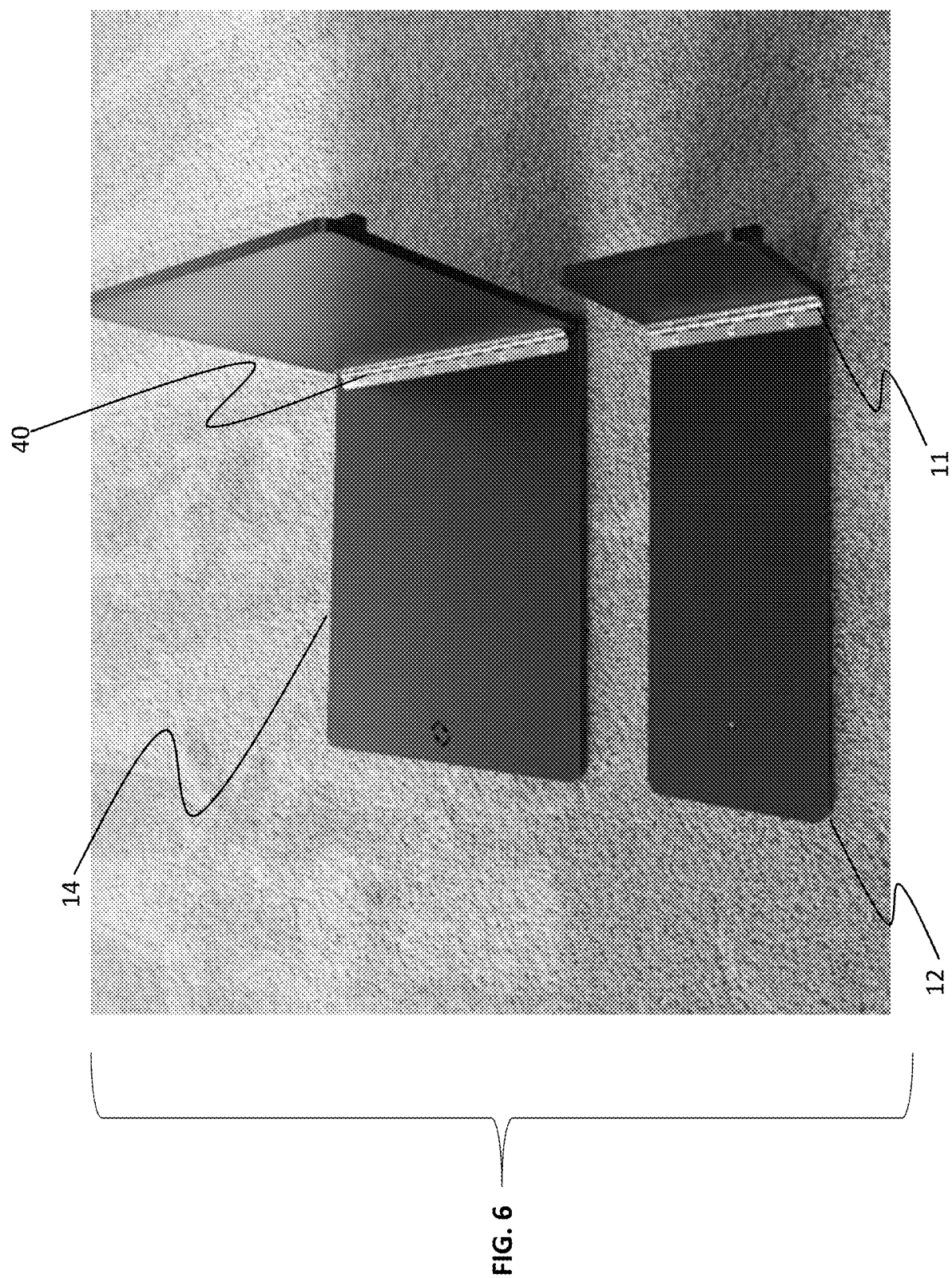
FIG. 6 shows an example of upper and lower assemblies in an open position.

Referring now to FIG. 6, an example of upper and lower assemblies each being in an open position is shown. The draw latches 60, 62 (as shown in FIG. 3) are used to secure a 90° angle between the upper and lower assemblies prior to attachment of the laser measurement device 20.

Figure 7:
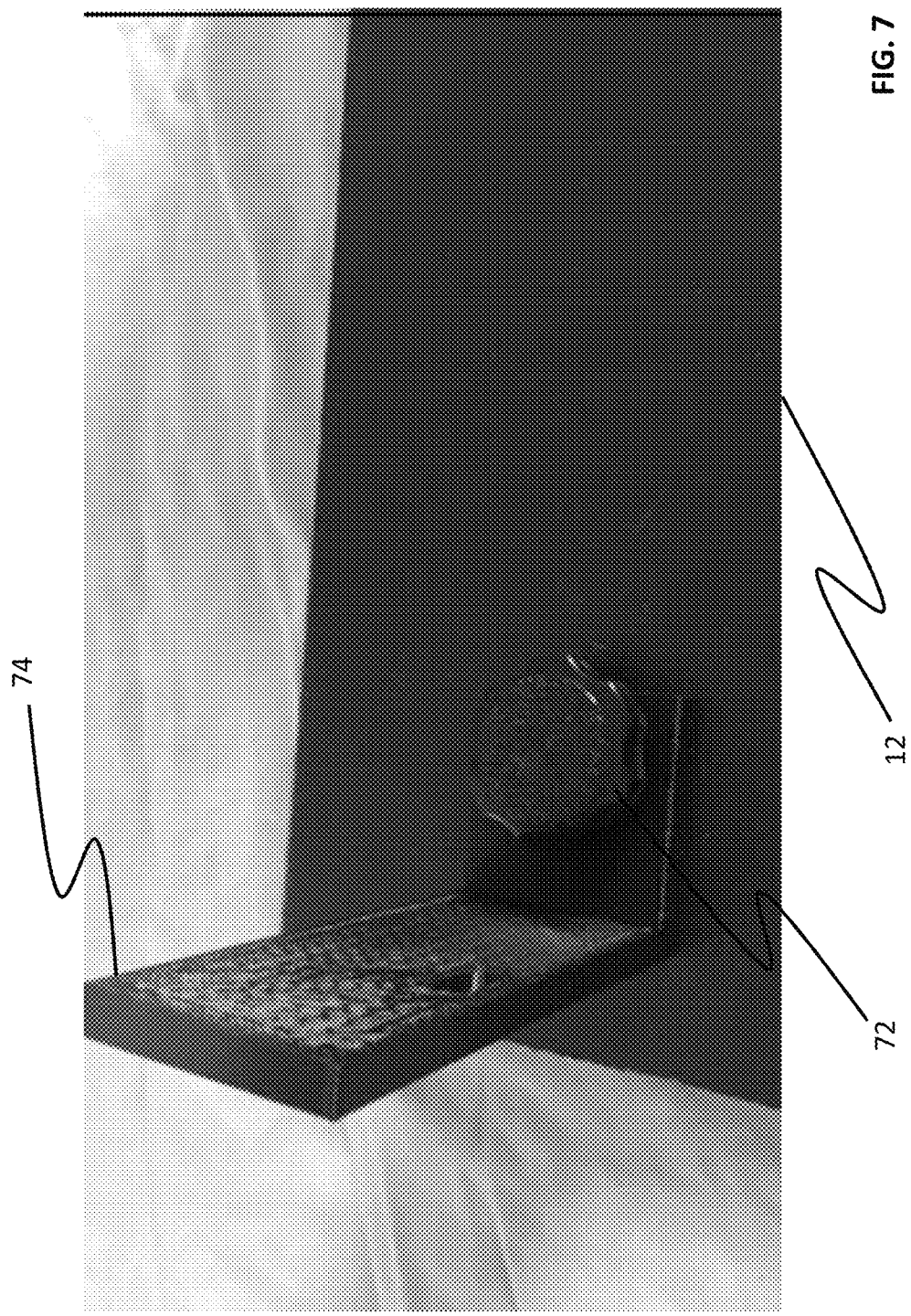
FIG. 7 shows an example of a laser base attached with a threaded knob to an upper assembly.

Referring now to FIG. 7, an example of a laser base attached with a tightening knob to an upper assembly is shown. In one example, the laser mounting base 74 may be mounted to the upper assembly 12, for example, by means of screwing attachment knob 72 into a mating threaded hole in the upper assembly 12.

Figure 8:
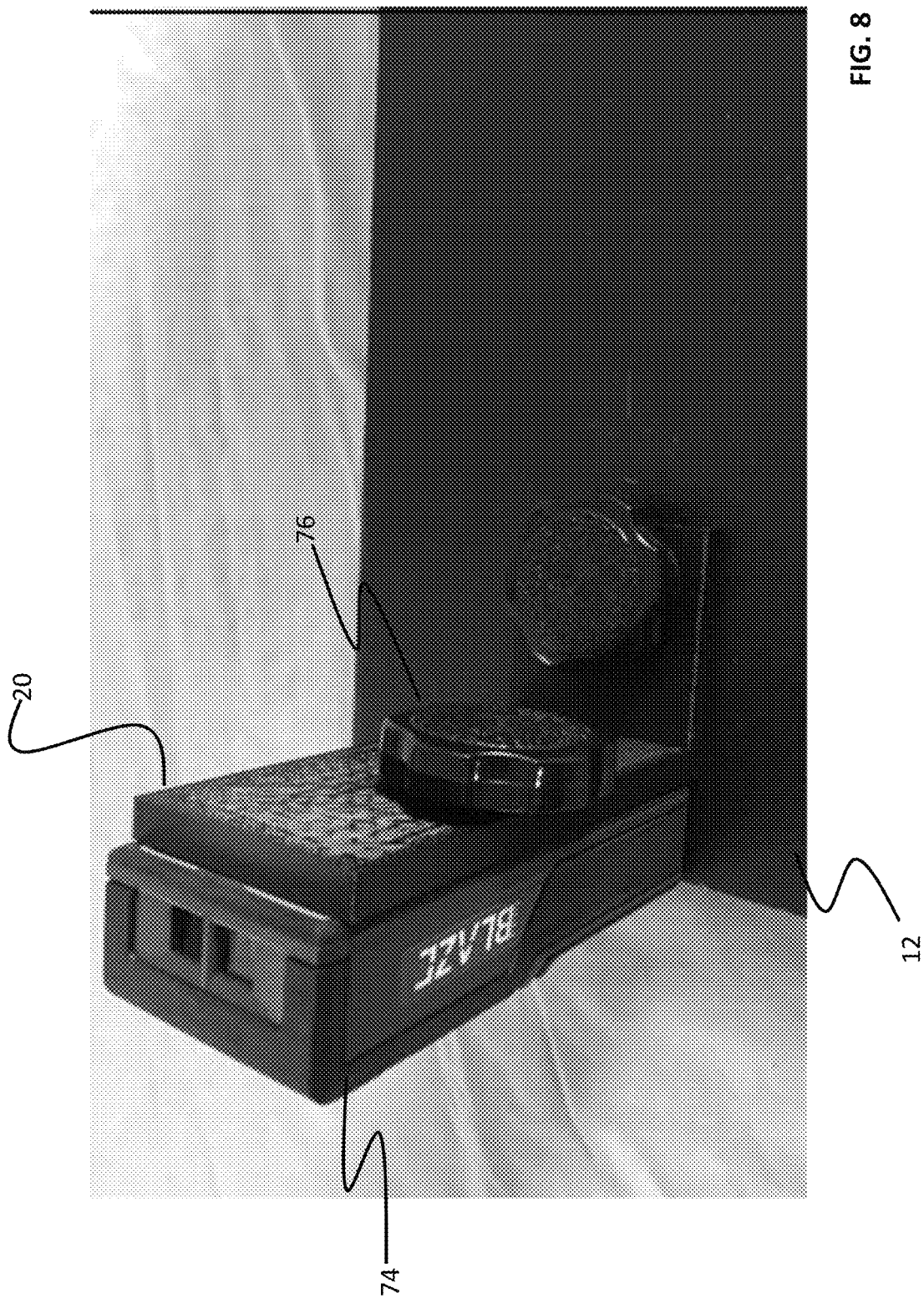
FIG. 8 shows an example of a laser attached to a base assembly which is attached to an upper assembly.

Referring now to FIG. 8, an example of a laser attached to a base assembly which is attached to an upper assembly is shown. Having attached the laser mounting base to the upper assembly 12, the laser may then be mounted to the mounting base 74 by means of an attachment knob 76. Laser measurement device 20 is mounted so as to have its functional buttons and display facing outward to be viewed by a user. The LAHI™ measuring device is ready for use. The laser is turned on and the beam is positioned to the center of the target on the lower assembly.

Experimental Examples

The inventors have conducted several human trials examining the validity and reliability of the laser height measurement devices. These trials were approved by the Institutional Review Board at Arizona State University, and all adult participants provided informed consent or, for the child measures, parental informed consent was obtained. An early first generation device (G1) consisted of a rectangular flat plate with a laser attached at the front underside and two levelers attached atop the back edges. The technician positioned the subject against a wall such that the back of the head, shoulder blades, buttocks, and heels touched the wall as outlined above. The device was placed on the head after any obscuring objects or hair buns were removed. The levelers were used to position the laser light perpendicular to the ground, and the laser was activated to display the distance which was manually written onto a spreadsheet. In a first human measurement trial, one technician assessed 57 children (aged 3-11 y) and 71 older individuals (12-80 years of age).[1]

The laser device measurement was conducted in triplicate to examine user reliability. The subject's height was also measured using a standard stadiometer to examine the validity of our device for measuring height. The mean heights, the standard deviations, and the error of the measurements are displayed in Table 1. In both the children and older individuals, the laser device proved valid for measuring height as indicated by the very strong intraclass correlation coefficients with the stadiometer measures (0.999 and 0.996 for the children and adults respectively). The stadiometer was operated by the technician in a reliable manner as indicated by the low measurement error (<1.2 mm). The laser device was slightly less reliable for measuring standing height with a measurement error ranging from 1.67 to 2.38 mm for the children and adults respectively.

TABLE 1

Height measurement (cm) using a novel laser device and a standard stadiometer in children (n = 57; 3-11 y) and older individuals (n = 71; 12-80 y)

| Measurement | Mean (cm) | SD (cm) | Measurement error (mm) |
| --- | --- | --- | --- |
| Child-laser | 149.172 | 0.289 | 1.67 |
| Child-stadiometer | 149.823 | 0.200 | 1.16 |
| Intraclass correlation | 0.999 | | |
| Adult-laser | 169.891 | 0.413 | 2.38 |
| Adult-stadiometer | 170.293 | 0.182 | 1.05 |
| Intraclass correlation | 0.996 | | |

A later version of the laser device (the second generation G2 laser device) was used in the following examples where the level was located on the underside of the plate to enable the technician to view the leveler from ground level. In addition, the steel plate was bent at a 90° angle allowing the device to be held against a wall to assure that the arm of the device holding the laser was parallel to the ground thus eliminating the need for the second leveler. The arm of the device that held the laser device for measuring height in adults was improved compared to the first generation device: 1.13 mm and 1.27 mm measurement error for technician 1 and 2 respectively compared to an error of 2.38 mm for the first generation device. The G2 laser device was also used to measure supine length by placing the upper assembly at the top of the head and the lower assembly at the bottom of the feet as depicted in FIG. 1. The leveler was used to position the laser light to hit the center of the lower assembly. The measurement error was 1.04 mm demonstrating the high reliability of this device in the hands of two technicians working independently (see Table 3).

Since there is no gold standard for measuring supine length, the inventors assessed this measure against arm span and knee height which are commonly used to estimate height in individuals unable to stand. For the arm span measurement the subject was told to raise their arms to a 90° angle from the torso. With the arms straight, a measurement was taken using a tape measure from fingertip to fingertip following the line of the shoulders.[2] Reportedly, arm span measures have the greatest variability in comparison to self-reported height, knee height, or recumbent length.[2] However, it is important to note that this variance was only seen for individuals with mobility issues; for those with no walking impairments across all ages, arm span was rated as a fairly accurate measure.[2] In another trial, the arm span measure yielded the lowest error, but only when applied for ages 18-40 y.[3] The knee height measure was taken with a knee height caliper and the participant sat upright and made a 90° angle with their knee, as measured by a goniometer. The caliper's fixed blade was placed on the far end of the calcaneus and the sliding blade on the anterior side of the distal condyles of the femur. For individuals who cannot lie completely flat, this estimate is considered the best estimation of standing height, although it may be more accurate for men than for women.[2] Findings from another study showed that knee height estimates became less reliable as the height increased.[4]

Table 3 displays the comparison of the supine measurement of the G2 laser device with arm span and knee height. It is clear that arm span is difficult to execute as measurement error ranged from 2.45 to 3.20 mm. Knee height measurements were reliably performed by both technicians operating independently (error: 0.48-0.71 mm). Intraclass correlations were strong for the supine length and knee height measures: 0.886 and 0.868. Both the supine length measurements using the G2 laser device and knee height calculations arrived at height values about 3 cm greater than standing height measures based on the stadiometer (171.1-171.4 cm vs. 168.2-168.3 cm respectively), suggesting that gravity and stature impact the standing measurement. It is also worthwhile to note that the laser devices measure standing height approximately 0.55 cm shorter than the stadiometer. In the only publication aside from ours (citation #1) that used a laser device to measure height, it was reported (in horses) that the laser device measured height below that recorded using a conventional measuring stick (−0.3 cm).[5] It is possible that since the laser device rests directly on the skull, it may compress the hair and skin to a greater degree than the stadiometer headpiece accounting for the shorter measurement.

TABLE 2

Standing height (cm) was measured by two technicians independently using the 2G laser device or a standard stadiometer. Supine length (cm) was assessed using the 2G laser device. (n = 80 adults; 18-71 y).

| Measurement | Device | Mean (cm) | SD (cm) | Measurement error (mm) |
|---|---|---|---|---|
| Standing height | | | | |
| Technician 1 | 2G laser device | 167.750 | 0.196 | 1.13 |
| | Stadiometer | 168.319 | 0.161 | 0.93 |
| | Intraclass correlation | 0.998 | | |
| Technician 2 | 2G laser device | 167.597 | 0.219 | 1.27 |
| | Stadiometer | 168.192 | 0.135 | 0.78 |
| | Intraclass correlation | 0.993 | | |

TABLE 3

Supine height was measured by two technicians independently using the 2G laser device or estimated using arm span and knee height. (n = 80 adults; 18-71 y).

| Measurement | Mean (cm) | SD (cm) | Measurement error (mm) | Standing height (cm) |
|---|---|---|---|---|
| Supine length | | | | |
| Technician 1 | 171.287 | 0.139 | 0.80 | 167.750 vs. 168.319[1] |
| Technician 2 | 171.008 | 0.181 | 1.04 | 167.597 vs. 168.192[1] |
| Arm span | | | | |
| Technician 1 | 168.780 | 0.555 | 3.20 | 167.700[2] |
| Technician 2 | 168.842 | 0.425 | 2.45 | 167.744[2] |
| Knee height | | | | |
| Technician 1 | 52.318 | 0.123 | 0.71 | 171.159[3] |
| Technician 2 | 52.464 | 0.083 | 0.48 | 171.426[3] |

[1]Height measured with 2G laser device vs. stadiometer from Table 2
[2]Calculated from arm span: male = 54.1 + [0.70 × AS] − [0.08 × age]; female: 43.1 + [0.75 × AS] − [0.08 × age]
[3]Calculated from knee height: males = 64.19 − (0.04 * age) + (2.02 * KH); females = 84.8 − (0.24 * age) + (1.83 * KH)

Certain exemplary embodiments of the invention have been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by different equipment, and devices, and that various modifications, both as to the equipment details and operating procedures, may be accomplished without departing from the true spirit and scope of the present invention.

In one example, a portable laser height measuring system includes an upper assembly including an elongated top flat plate attached to an upper back plate, wherein the elongated top flat plate includes a top side and an underside. A separate lower assembly including a base is attached to a bottom backplate. A laser measurement device is affixed to the elongated top flat surface. A leveling device may be mounted at one end of the elongated top flat plate proximate the laser measurement device; and a data collection device electronically coupled to receive signals from the laser measurement device wherein the upper assembly is adapted to be placed on a subject's head and is aligned with the lower assembly which is adapted to be used as a platform for a subject's feet such that the laser measurement device is aligned with the target.

In one example, the laser measurement device wirelessly transmits data to the data collection device.

In another example, the laser measurement device is removably affixed to the underside of the elongated top flat surface.

In another example, the elongated top flat plate is attached to the upper backplate with an upper hinge.

In another example, the base is attached to the bottom backplate with a lower hinge.

In another example, the data collection device is selected from the group consisting of a personal computer, smart phone, computer, computer tablet and laptop computer.

In another example, a method for measuring height of a standing subject having a head, heels and feet, the method includes the acts of placing an upper assembly including an elongated top flat plate attached to an upper back plate, wherein the elongated top flat plate includes a top side and an underside, on top of the head; positioning the upper backplate vertically against a wall; mounting a laser measuring device at one end of the elongated top flat plate with the laser beam pointed toward the ground; mounting a leveler proximate the one end of the elongated top flat plate; causing the individual to stand against a wall or to be freestanding; positioning a base and having the individual place their feet on the base, if a wall is used, having the individual's heel be firmly touching the backplate and the back of the head, shoulder blades and buttocks firmly touching the wall; positioning the upper assembly on top of the head with the upper back plate behind the individual's head and against the wall; adjusting the individual's head to align with the Frankfort plane; aligning the laser measuring device may with a target; and then activating the laser measuring device to acquire a height measurement.

In another example, the method includes electronically coupling a data collection device to receive signals from the laser measurement device.

In another example, the method includes activating the laser measurement device to wirelessly transmit data to the data collection device.

In another example, the laser measurement device is removably mounted.

In another example, the method includes attaching the elongated top flat plate to the upper backplate with an upper hinge.

In another example, the method includes attaching the base to the bottom backplate with a lower hinge.

In yet another example, the data collection device is selected from the group consisting of a personal computer, smart phone, computer, computer tablet and laptop computer.

In another example, the method includes averaging a plurality of height measurements of the same individual.

In another aspect, a method for measuring height of a supine subject having a head, heels and feet, the method includes causing the individual to assume a supine position on a surface; placing an upper assembly including an elongated top flat plate attached to an upper back plate, wherein the elongated top flat plate includes a top side and an underside, on top of the head; positioning the upper backplate onto the surface at the back of the head; mounting a laser measuring device at one end of the elongated top flat plate with the laser beam pointed toward the feet; mounting a leveler proximate the one end of the elongated top flat plate; positioning a base having a target, having the individual place their feet against the base, having the individual's heel be firmly touching the backplate and the back of the head, shoulder blades and buttocks firmly touching the surface; positioning the upper assembly on top of the head with the upper back plate behind the individual's head and against the wall; adjusting the individual's head to align with the Frankfort plane; aligning the laser measuring device with the target; and then activating the laser measuring device to acquire a height measurement.

What is claimed is:

1. A portable laser height measuring system, the system comprising:
   an upper assembly including an elongated top flat plate foldably coupled to an upper backplate by an upper hinge, wherein the elongated top flat plate includes a top side and an underside;
   a separate lower assembly including a base foldably coupled to a bottom backplate by a lower hinge, wherein the lower assembly includes a target, and wherein in use of the portable laser height measuring system, the lower assembly is configured to not be physically connected to the upper assembly;
   a laser measurement device affixed to the elongated top flat surface and comprising a laser, wherein the laser generates a laser beam when activated; and
   a data collection device electronically coupled to receive signals from the laser measurement device wherein the upper assembly is adapted to be placed on a subject's head and is aligned with the lower assembly which is adapted to be used as a platform for a subject's feet such that the laser measurement device is aligned with the target.

2. The portable laser height measuring system of claim 1 wherein the laser measurement device includes a wireless transmitter configured for wirelessly transmitting data to the data collection device.

3. The portable laser height measuring system of claim 1 wherein the laser measurement device is removably affixed to the underside of the elongated top flat surface.

4. The portable laser height measuring system of claim 1 wherein the data collection device is selected from the group consisting of a personal computer, a smart phone, a tablet computer, and a laptop computer.

5. The portable laser height measuring system of claim 1 further comprising a target indentation located at one end of the base and configured to guide the laser beam perpendicular to a ground surface.

6. The portable laser height measuring system of claim 1 wherein the elongated top flat plate is adapted for affixing a leveling device mounted at one end of the elongated top flat plate proximate the laser measurement device.

7. A method for measuring height of a standing subject having a head, heels and feet utilizing the portable laser height measuring system of claim 1, the method comprising:
   placing the upper assembly on top of the head of the standing subject,
   positioning the upper backplate vertically against a wall;
   pointing the laser measurement device toward a ground surface underlying feet of the standing subject;
   mounting a leveler proximate to an end of the elongated top flat plate;
   having the standing subject place the subject's feet on the base;
   positioning the upper assembly on top of the head of the standing subject with the upper backplate behind the subject's head;
   adjusting the subject's head to align with the Frankfort plane;
   aligning the laser measuring device with the target; and
   activating the laser measuring device to acquire a height measurement of the standing subject.

8. The method of claim 7 further comprising wirelessly transmitting data from the laser measurement device to the data collection device.

9. The method of claim 7 wherein the laser measurement device is removably affixed to the elongated top flat surface.

10. The method of claim 7 wherein the data collection device is selected from the group consisting of a personal computer, a smart phone, a tablet computer, and a laptop computer.

11. The method of claim 7 further comprising averaging a plurality of height measurements of the same standing subject.

12. A method for measuring height of a supine subject having a head, heels and feet utilizing the portable laser height measuring system of claim 1, the method comprising:
   causing the individual to assume a supine position on a surface;
   placing the upper assembly on top of the head of the supine subject,
   positioning the upper backplate onto the surface at a back of the head of the supine subject;
   pointing the laser measurement device toward the feet of the supine subject;

mounting a leveler proximate to an end of the elongated top flat plate;

having the supine subject place the subject's feet against the base;

positioning the upper assembly on top of the head of the supine subject with the upper backplate behind the subject's head wall;

adjusting the subject's head to align with the Frankfort plane;

aligning the laser measuring device with the target; and activating the laser measuring device to acquire a height measurement of the supine subject.

13. The method of claim 12 further comprising wirelessly transmitting data from the laser measurement device to the data collection device.

14. The method of claim 12 wherein the laser measurement device is removably affixed to the elongated top flat surface.

15. The method of claim 12 further comprising averaging a plurality of height measurements of the same supine subject.

\* \* \* \* \*